(12) United States Patent
Hunt et al.

(10) Patent No.: US 8,602,988 B2
(45) Date of Patent: Dec. 10, 2013

(54) RECOVERY DETERMINATION METHODS AND RECOVERY DETERMINATION APPARATUSES

(75) Inventors: Jeff Hunt, Concord, MA (US); Matthew Weatherly-White, Boise, ID (US)

(73) Assignee: Recovery Science and Technology, LLC, Concord, MA (US)

( * ) Notice: Subject to any disclaimer, the term of this patent is extended or adjusted under 35 U.S.C. 154(b) by 750 days.

(21) Appl. No.: 12/698,964

(22) Filed: Feb. 2, 2010

(65) Prior Publication Data

US 2011/0190645 A1    Aug. 4, 2011

(51) Int. Cl.
*A61B 5/02* (2006.01)
*A61B 5/00* (2006.01)

(52) U.S. Cl.
USPC .......................... 600/301; 600/300; 600/500

(58) Field of Classification Search
USPC .......................................... 600/500; 482/1–9
See application file for complete search history.

(56) References Cited

U.S. PATENT DOCUMENTS

| | | | |
|---|---|---|---|
| 5,297,558 A | 3/1994 | Acorn et al. | |
| 5,479,592 A | 12/1995 | Stenhouse | |
| 5,598,849 A | 2/1997 | Browne | |
| 6,013,007 A | 1/2000 | Root et al. | |
| 6,043,294 A | 3/2000 | Hed | |
| 6,104,947 A * | 8/2000 | Heikkila et al. | 600/519 |
| 6,461,162 B1 | 10/2002 | Reitman et al. | |
| 6,516,222 B2 * | 2/2003 | Fukuda | 600/547 |
| 6,534,487 B1 | 3/2003 | Kaufman | |
| 6,687,535 B2 * | 2/2004 | Hautala et al. | 600/520 |
| 6,904,313 B1 | 6/2005 | Snell | |
| 7,043,294 B1 | 5/2006 | Paris | |
| 7,107,095 B2 | 9/2006 | Manolas | |
| 7,153,250 B2 | 12/2006 | Takizawa et al. | |
| 7,192,401 B2 | 3/2007 | Saalasti et al. | |
| 7,396,127 B2 | 7/2008 | Bae et al. | |
| 7,567,693 B2 | 7/2009 | deCharms | |
| 7,603,255 B2 | 10/2009 | Case, Jr. et al. | |
| 7,641,592 B2 | 1/2010 | Roche | |
| 7,753,825 B2 | 7/2010 | Jaquish et al. | |
| 7,775,937 B2 | 8/2010 | Jaquish et al. | |
| 7,780,574 B2 | 8/2010 | Jaquish et al. | |
| 7,806,806 B2 | 10/2010 | Jaquish et al. | |
| 7,959,540 B2 | 6/2011 | Jaquish et al. | |
| 7,981,002 B2 | 7/2011 | Roche | |
| 2001/0027266 A1 * | 10/2001 | Hautala et al. | 600/16 |
| 2004/0010420 A1 | 1/2004 | Rooks | |

(Continued)

OTHER PUBLICATIONS

Mackenzie, B. (2000) Over Training. http://web.archive.org/web/20080701101429/http://www.brianmac.co.uk/overtrn.htm.*

(Continued)

*Primary Examiner* — Navin Natnithithadha
*Assistant Examiner* — Meredith Weare
(74) *Attorney, Agent, or Firm* — Wells St. John P.S.

(57) ABSTRACT

Recovery determination methods and recovery determination apparatuses are described. According to one aspect, a recovery determination method includes accessing an input for a recovery marker which corresponds to a characteristic of an individual, wherein the input comprises data pertinent to the individual for the recovery marker while the individual is at rest following a period of exercise by the individual, processing the data of the individual for the recovery marker, and determining recovery information which is indicative of a state of recovery of the individual using the processing.

19 Claims, 4 Drawing Sheets

(56) References Cited

U.S. PATENT DOCUMENTS

| | | |
|---|---|---|
| 2004/0267565 A1 | 12/2004 | Grube |
| 2005/0080344 A1* | 4/2005 | Nishii et al. .................. 600/483 |
| 2006/0032315 A1* | 2/2006 | Saalastic et al. ............... 73/808 |
| 2006/0250524 A1 | 11/2006 | Roche |
| 2007/0042972 A1 | 2/2007 | McKeever et al. |
| 2007/0087913 A1* | 4/2007 | Jaquish et al. ................. 482/91 |
| 2007/0276282 A1 | 11/2007 | Fukumura et al. |
| 2008/0146415 A1* | 6/2008 | Takizawa et al. ................ 482/8 |
| 2009/0062627 A1 | 3/2009 | Younger |
| 2009/0269728 A1* | 10/2009 | Verstegen et al. ............. 434/247 |
| 2009/0275442 A1* | 11/2009 | Nissila .............................. 482/4 |
| 2010/0113226 A1 | 5/2010 | Jaquish et al. |
| 2010/0137108 A1 | 6/2010 | Jaquish et al. |
| 2010/0137109 A1 | 6/2010 | Jaquish et al. |
| 2010/0173750 A1 | 7/2010 | Roche |
| 2011/0015042 A1 | 1/2011 | Jaquish et al. |

OTHER PUBLICATIONS

Anderson, O. (2002) How do you know when you are at risk of overtraining? It's a simple matter of well you feel, sleep and eat. Peak Performance, 163, p. 1-4.*
Kentta et al. (1998) Overtraining and Recovery: A Conceptual Model. Sports Medicine, 26(1), p. 1-16.*
Kellmann, M. (2002). Underrecovery and overtraining: Different concepts—similar impact? In M. Kellmann (Ed.), Enhancing recovery: Preventing underperformance in athletes (pp. 3-24).*
Calder, A. (2005). Recovery Training. Australian Institute of Sport. 23 pages.*
Bishop et al. (2008). Recovery from Training: A Brief Review. Journal of Strength and Conditioning Research, 22, 3. pp. 1015-1024.*
Hooper et al. "Markers for Monitoring Overtraining and Recovery." Med Sci Sports Exerc. Jan. 1995;27(1):106-12.*
Robson-Ansley et al. "Fatigue management in the preparation of Olympic athletes." Journal of Sports Sciences, 27:13, 1409-1420.*
"Statistical Graphs." http://math.youngzones.org/stat_graph.html.*
"Bar Graphs." (2004) http://www.ncsu.edu/labwrite/res/gh/gh-bargraph.html.*
Wilson, James. Rest & Recovery: The Overlooked Aspect of Training Success: Part 2. May 25, 2009. http://web.archive.org/web/20090525080235/http://www.bodybuilding.com/fun/issa71.htm?*
Bompa et al. "Chapter 5: Rest and Recovery." Periodization: Theory and Methodology of Training. Aug. 10, 2009. pp. 97-122.*
Mackenzie, B. Dec. 19, 2008. http://web.archive.org/web/20081219134521/http://www.brianmac.co.uk/overtrn.htm.*
"Graphing Resources: Bar Graphs." LabWrite. (2004) http://www.ncsu.edu/labwrite/res/gh/gh-bargraph.html.*
Allen et al. "Photoplethysmography detection of lower limb peripheral arterial occlusive disease: a comparison of pulse timing, amplitude and shape characteristics." Physiol. Meas. 26 (2005) 811-821.*
"Physical Overtraining." ExRx.net. Apr. 16, 2009. http://web.archive.org/web/20090416105121/http://www.exrx.net/ExInfo/Overtraining.html.*
Robson-Ansley et al. "Fatigue management in the preparation of Olympic athletes." Journal of Sports Sciences, 27:13, Feb. 16, 2009, pp. 1409-1420.*
"Statistical Graphs." Feb. 13, 2009. http://math.youngzones.org/stat_graph.html.*
PCT/US2011/023034, Sep. 27, 2011, Search Report.
PCT/US2011/023034, Sep. 27, 2011, Written Opinion.
PCT/US2011/023034, Aug. 7, 2012, IPRP.
Kingsbury et al.; Contrasting plasma free amino acid patterns in elite athletes: association with fatigue and infection; 1998; pp. 25-33.
Lamberts et al.; Day-To-Day Variation in Heart Rate at Different Levels of Submaximal Exertion: Implications for Monitoring Training; May 2009; pp. 1005-1010.
Locke et al.; Persistent fatigue in young athletes: measuring the clinical course and identifying variables affecting clinical recovery; 2009; pp. 1-8.
Lamberts et al.; Heart rate recovery as a guide to monitor fatigue and predict changes in performance parameters; 2009; pp. 1-9.
Achten et al.; Heart Rate Monitoring, Applications and Limitations; 2003; pp. 517-538.
Coutts et al.; Practical tests for monitoring performance, fatigue and recovery in triathletes; Feb. 2, 2007; pp. 372-381.
Recovery and Regeneration; http://web.archive.org/web/20090217083017/http:nvo.com/sportquestdir/recovery; 1997 2 pp.
Alves et al.; Monitoring and prevention of overtraining in athletes; 2006; pp. 262e-266e.
Borresen et al.; The Qualification of Training Load, the Training Response and the Effect on Performance; 2009; pp. 779-795.
Halson et al.; Does Overtraining Exist? An Analysis of Overreaching and Overtraining Research; 2004; pp. 967-981.
Gazzano, F.; The Overtraining Syndrome Detection and Prevention; 2006; pp. 1-14.
Hansen, D.; Identifying and Managing Fatigue in Running Athletes—Part 1; Feb. 10, 2009; 5 pp.
Perna et al.; Role of Psychological Stress in Cortisol Recovery from Exhaustive Exercise Among Elite Atheletes; Int'l Journal of Behavioral Medicine; 1995; pp. 13-26.
Sharp et al.; Monitoring your athletes vs overtraining; Jan. 2007; 2 pp.
Quantifying Stress with Stress Score with CPT Premier Coach, Rick Crawford; http://coloradopremiertraining.com/news/cns/about.php; 2002; 2 pp.
Heart Beat Based Recovery Analysis for Athletic Training; Firstbeat Technologies Ltd.; Mar. 2009; pp. 1-4.
Gustafsson et al.; An elite endurance athelte's recovery from under performance aided by a multidisiplinary sport science support team; Sep. 2008; pp. 267-276.
Urhausen et al.; Diagnosis of Overtraining, What Tools Do We Have?; 2002; pp. 95-102.
Budgett et al.; The effects of the 5-HT2c agonist m-chlorophenlpiperazine on elite atheltes with unexplained underperformance syndrome (overtraining); May 28, 2008; 4 pp.
Gleeson, M.; Biochemical and Immunological Markers of Over-Training; Jun. 1, 2002; pp. 31-41.
Bagger et al.; Biological Variation in Variables Associated with Exercise Training; 2003; pp. 433-440.
Meeusen et al.; Hormonal Responses in athletes: the use of a two bout exercise protocol to detect subtle differentces in (over) training status; Oct. 2, 2003; pp. 140-146.
Wu et al.; Hormonal responses in heavy training and recovery periods in an elite male weightlifter; Dec. 1, 2008; 2 pp.
Waldeck et al.; Heart Rate During Sleep: Implications for Monitoring Training Status; Dec. 1, 2003; pp. 133-138.
Meeusen et al.; Prevention, diagnosis and treatment of the Overtraining Syndrome ECSS Position Statement 'Task Force'; Mar. 2006; pp. 1-14.
Vaananen, I.; Physiological Responses and Mood States After Daily Repeated Prolonged Exercise; Journal of Sports Science & Medicine; vol. 3; 2004; pp. 1-43.
Lane et al.; Mood Distrubance During Cycling Performance at Extreme Conditions; Mar. 1, 2005; pp. 52-57.
Montgomery et al.; Using Heart Rate Variability to Help Your Athletic Performance; FitSense Austrailia; 2005; pp. 16-26.
Kudielka et al.; Why do we respond so differently? Reviewing determinants of human salivary cortisol responses to challenge; Oct. 2008; pp. 2-18.
Main et al.; Relationship Between Inflammatory Cytokines and Self-Report Measures of Training Overload; Jun. 12, 2009; pp. 127-139.
Rushall, B.; A Tool for Measuring Stress Tolerance in Elite Athletes; 1993; pp. 51-66.
Coutts et al.;Changes in Selected Biochemical, Muscular Strength, Power and Endurance Measures during Deliberate Overreaching and Tapering in Rugby League Players; 2006;pp. 1-9.
Maleska et al.; The changes of ACTH, cortisol, testosterone and testosterone/cortisol ration in professional soccer players during a competition half-season; 2006; pp. 259-263.
Vernacchia, R.; Psychological Restoration: Assessing Underrecovery and Underperforming in Tack and Field Athletes; 2007; 6 pp.

(56) References Cited

OTHER PUBLICATIONS

Hartwig et al.; Load stress, and recovery in adolescent rugby union players during a competitive season; Aug. 2009; pp. 1087-1094.
Maffetone, P.; The Overtraining Syndrome; 2007; pp. 1-4.
Impellizzer et al.; Use of RPE-Based Training Load in Soccer; 2004; pp. 1042-1047.
Tanskanen et al.; Altered Oxidative Stress in Overtrained Athletes; Feb. 1, 2010; pp. 309-317.
Carling et al.; Performance Assessment for Field Sports; Chapter 8, 2009; pp. 200-217.
Rietjens et al.; Phsiological, Biochemical and Psychological Markers of Strenuous Training-Induced Fatigue; Sep. 10, 2004; pp. 16-26.
Anderson,; How to balance intensive training with rest and recovery; 2009; http://www.pponline.co.uk/encyc/how-to-balance-intensive-training-with-rest-and-recovery-269; 5 pp.
Brown, C. Harmon; Part 1—Principles of Training; International Association of Athletics Federations Medical Manual; May 2009; 14 pp.
Goldsmith, Wayne; Recovery Based Traning—An Alternate Method of Athelte Preperation; www.swimmingcoach.org/articles/JL10102002.asp; 1999; 10 pp.
Anderson, Owen; Swimming, overtraining, recovery and norepinephrine; www.pponline.co.uk/encyc/recovery.html; 2008; 9 pp.
Clarkson et al.; Exercise-Induced Muscle Damage in Humans; Am J Phys. Med. rehabil., vol. 81, No. 11 (Suppl); Nov. 2002; pp. S52-S69.
Jenkins, Mark; The Overtraining Syndrome; www.rice.edu/~jenky/sports/overtraining.html; 1998; 3 pp.
Weil et al.; Muscle Soreness; www.medicinenet.com/script/main/art.asp?articlekey=78966; 1996; 3 pp.
Cluett, J.; Muscle Soreness After Exercise; http://orthopedics.about.com/od/overuseinjuries/qt/soremuscle.htm; Nov. 23, 2009; 1 pp.
Connolly et al.; treatment and prevention of delayed onset muscle soreness; www.ncbi.nlm.nih.gov/pubmed/12580677; Feb. 2003; 1 pp.
Ryan, M.; Monique Ryan: Books & Products; www.moniqueryan.com/books/books.html; 2007; 2 pp.
Sports Nutrition: Energy Metabolism and Exercise (Nutrition in Exercise & Sport); www.amazon.com/Sports-Nutrition-Energy-Metabolism-Exercise/dp/0849379504; Sep. 2007; 5 pp.
Profile of Mood States; Nov. 24, 2009; 2 pp; http://www.statistics-solutions.com/methods-chapter/directory-of-survey-instruments/profile-of-mood-states.
Iocchelli, M.; The What, Why & How of Your Resting Heart Rate; http://completerunning.com/archives/2006/11/01/resting-heart-rate; 2007; 5 pp.
Maes et al.; Treating and Preventing DOMS; http://www.unm.edu/~lkravitz/Article%20folder/domos.html; 2003; 4 pp.
Tiidus, Peter; Skeletal Muscle Damage and Repair; 2008; 346 pp.
Meeusen, Romain; The Overtraining Syndrome: Diagnosis and Management; Chpt. 3; 2008.
Maughan et al., Overreaching and Overtraining; In the Biochemical basis of sports performance; 2004; p. 209-211.
Kuipers et al.; Overtraining, in Hargreaves, M. & Hawley, J. (Eds); Physiological bases of sports performance; Chpt. 6; 2003; p. 108-121.
Profile of Mood States; www.answers.com/topic/profile-of-mood-states; 1980; 2 pp.
Characteristics of Sports Research Using the Profile of Mood States; www.questia.com/library/1G1-16514206/characteristics-of-sports-research-using-the . . . Nov. 23, 2009; 2 pp.

* cited by examiner

RECOVERY DETERMINATION METHODS AND RECOVERY DETERMINATION APPARATUSES

TECHNICAL FIELD

This disclosure relates to recovery determination methods and recovery determination apparatuses.

BACKGROUND OF THE DISCLOSURE

An athlete's training program consists of two parts including a stimulus phase and a rest phase. Training stimulus triggers a physiological response in the body. During rest, the body responds to the training stimulus through adaptation, thus preparing itself to perform the same activity more effectively and efficiently in the future. In other words, the athlete gets fitter and can perform at a higher level. These gains occur during the rest phase. If there is not adequate rest, an athlete's body can not sufficiently repair itself and the athlete is not able to improve performance in subsequent training sessions or races and performance may deteriorate in the absence of adequate recovery.

It is often desired to balance effort with rest and recovery for a successful training regimen. Too much rest means the athlete is not stressing his body as much as he could and therefore is not gaining as much fitness as possible; too little rest means the athlete does not achieve the adaptive gains from the stress. Many athletes constantly struggle to find this important balance and the question that most coaches and athletes aim to answer is how hard to push and how much to rest and being able to successfully determine this fine line can often be the difference between winning and losing.

Due to the widespread use of scientifically proven tools which measure training stimulus, elite athletes rarely struggle to define the intensity, duration or volume of training stimulus that they execute. However, athletes typically struggle to define the amount of recovery to adapt to this training stimulus. High training loads without adequate recovery will result in reduced performance, which if continued for a prolonged period can lead to chronic fatigue and overtraining syndrome.

At least some aspects of the disclosure are directed to methods and apparatus for determining states of recovery of individuals.

BRIEF DESCRIPTION OF THE DRAWINGS

Exemplary embodiments of the disclosure are described below with reference to the following accompanying drawings.

DETAILED DESCRIPTION OF THE DISCLOSURE

This disclosure is submitted in furtherance of the constitutional purposes of the U.S. patent Laws "to promote the progress of science and useful arts" (Article 1, Section 8).

According to one embodiment, a recovery determination method comprises accessing an input for a recovery marker which corresponds to a characteristic of an individual, wherein the input comprises data pertinent to the individual for the recovery marker while the individual is at rest following a period of exercise by the individual, processing the data of the individual for the recovery marker, and determining recovery information which is indicative of a state of recovery of the individual using the processing.

According to an additional embodiment, a recovery determination method comprises accessing a plurality of inputs for respective ones of a plurality of different recovery markers which correspond to respective ones of a plurality of different characteristics of an individual, wherein the inputs comprise data pertinent to the individual for respective ones of the recovery markers, processing the data for the respective ones of the recovery markers, and using the processing, determining recovery information regarding a state of recovery of the individual after a period of exercise by the individual.

According to another embodiment, a recovery determination apparatus comprises an interface configured to receive an input for a recovery marker which corresponds to a characteristic of an individual, wherein the input comprises data pertinent to the individual for the recovery marker while the individual is at rest following a period of exercise by the individual, and processing circuitry coupled with the interface and configured to receive the data for the recovery marker, process the data for the recovery marker, and determine recovery information which is indicative of a state of recovery of the individual using the processing.

Methods and apparatus for determining the recovery of an individual are described below according to some aspects of the disclosure. In one example, the individual may be an athlete who wishes to use recovery information generated by the methods and apparatus of the disclosure and which indicates a state or level of recovery of the individual to assist with a training program for the individual. More specifically, in one aspect, the individual may provide data regarding one or more recovery markers and the methods and apparatus of the disclosure may provide recovery information in return which is indicative of the individual's state of recovery following a period of exertion (e.g., a training workout) performed by the individual. In further example aspects, the individual may use the recovery information to determine whether they are sufficiently recovered to resume training or whether they are not sufficiently recovered and should rest an additional amount of time before resuming exercise.

Figure 1:
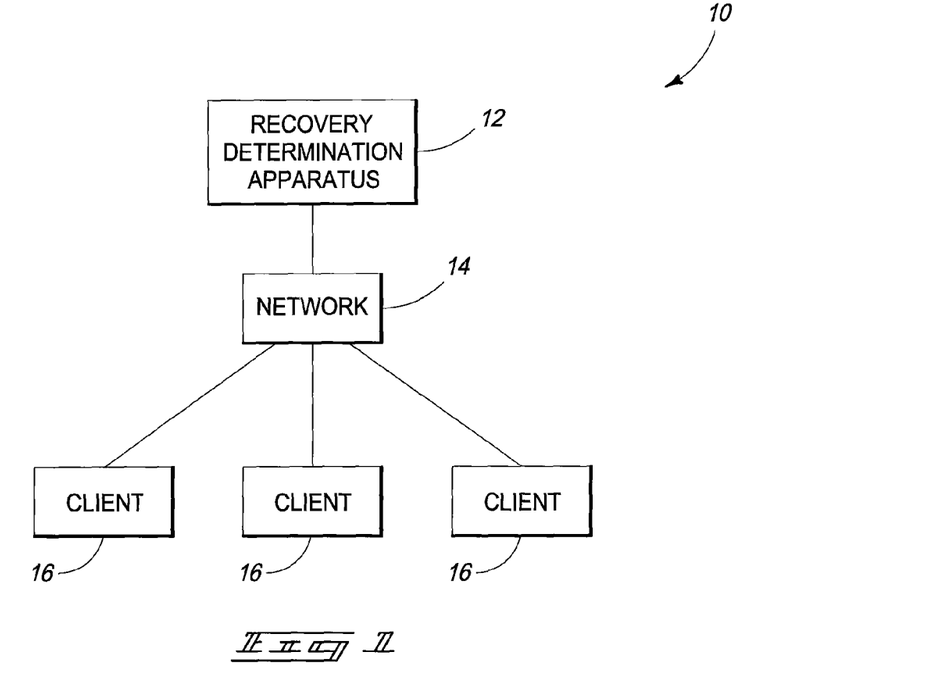
FIG. 1 is a functional block diagram of a system configured to implement at least some aspects of the disclosure according to one embodiment.

Referring to FIG. 1, some aspects of the disclosure are described with respect to a system 10 depicted according to one example embodiment. The system 10 includes a recovery determination apparatus 12, a network 14 and a plurality of clients 16 (e.g., which may be personal computers or other appropriate devices arranged to communicate with apparatus 12) in the depicted embodiment.

The recovery determination apparatus 12 may be embodied as a server which is configured to serve web pages to clients 16. In addition, recovery determination apparatus 12 may perform processing of data entered by individuals interacting with clients 16 to calculate respective recovery information for the individuals as described below and which is indicative of the individuals' respective states of recovery at moments in time corresponding to the entry of the data. Other aspects of apparatus 12 are described below.

Network 14 comprises any suitable medium (e.g., Internet, wide area networks, and/or local area networks) for communicating data intermediate the recovery determination apparatus 12 and the clients 16. Other configurations are possible.

For example, in another embodiment, software may be provided to individuals who install the software on their respective computers for use in practicing recovery determination aspects described in this disclosure without use of or communication to an external server or other computer. In such an example arrangement, the computer of the individual may be considered to be the recovery determination apparatus 12 and such an apparatus 12 need not communicate with external devices, such as a server, to implement aspects of the disclosure. The recovery determination apparatus 12 may be embodied in other configurations in other embodiments (e.g., personal computing devices, cellular phones, etc.). Some aspects of the disclosure described below pertain to the configuration of system 10 shown in FIG. 1 where the apparatus 12 is implemented as a server although other aspects are not limited to this described example.

Figure 2:
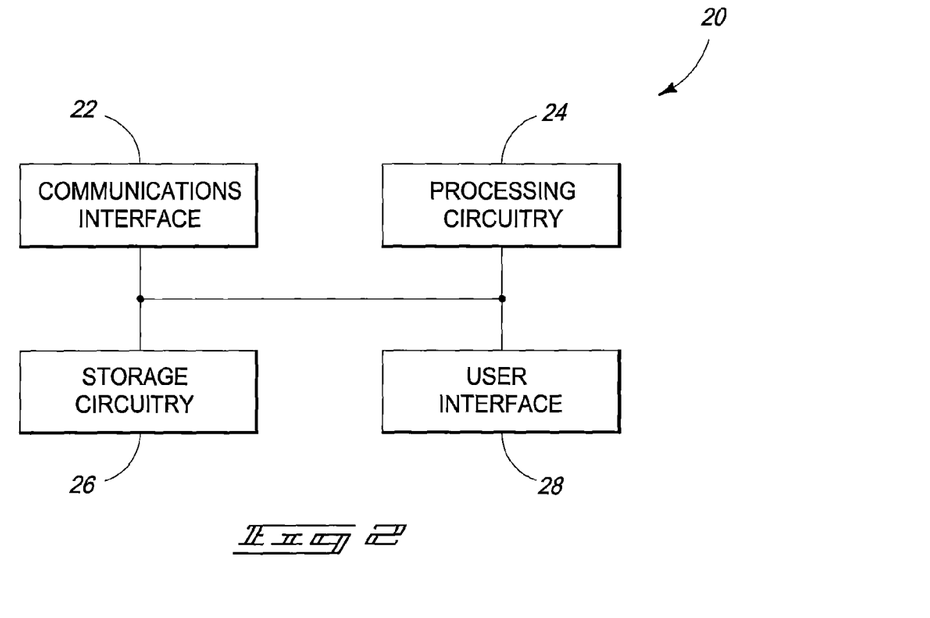
FIG. 2 is a functional block diagram of a computing device according to one embodiment.

Referring to FIG. 2, one embodiment of a computing device 20 is shown. In one implementation, recovery determination apparatus 12 implemented as a server is configured as the described computing device 20. Clients 16 may also be individually implemented as a computing device 20. In accordance with some embodiments mentioned above, the computing device 20 of an individual may be configured as the recovery determination apparatus without communications to a network or remote server.

Computing device 20 includes a communications interface 22, processing circuitry 24, storage circuitry 26, and a user interface 28 in the depicted example. Other embodiments of computing device 20 are possible including more, less and/or alternative components.

Communications interface 22 is arranged to implement communications of computing device 20 with respect to external devices. For example, communications interface 22 may be arranged to communicate information bi-directionally with respect to network 14. Communications interface 22 may be implemented as a network interface card (NIC), serial or parallel connection, USB port, Firewire interface, flash memory interface, floppy disk drive, or any other suitable arrangement for communicating with respect to computing device 20 and remote devices.

Processing circuitry 24 may comprise circuitry configured to implement desired programming provided by appropriate media in at least one embodiment. For example, the processing circuitry 24 may be implemented as one or more of a processor, controller and/or other structure configured to execute executable instructions including, for example, software and/or firmware instructions, and/or hardware circuitry. Exemplary embodiments of processing circuitry 24 include hardware logic, PGA, FPGA, ASIC, state machines, and/or other structures alone or in combination with a processor. These examples of processing circuitry 24 are for illustration and other configurations are possible.

The storage circuitry 26 is configured to store programming such as executable code or instructions (e.g., software and/or firmware), electronic data, databases, image data, or other digital information and may include processor-usable media. Processor-usable media may be embodied in any computer program product(s) or article of manufacture(s) which can contain, store, or maintain programming, data and/or digital information for use by or in connection with an instruction execution system including processing circuitry in the exemplary embodiment. For example, exemplary processor-usable media may include any one of physical media such as electronic, magnetic, optical, electromagnetic, infrared or semiconductor media. Some more specific examples of processor-usable media include, but are not limited to, a portable magnetic computer diskette, such as a floppy diskette, zip disk, hard drive, random access memory, read only memory, flash memory, cache memory, and/or other configurations capable of storing programming, data, or other digital information.

At least some embodiments or aspects described herein may be implemented using programming stored within appropriate storage circuitry 26 described above and configured to control appropriate processing circuitry 24. For example, programming may be provided via appropriate articles of manufacture including, for example, embodied within media discussed above.

User interface 28 is configured to interact with a user including conveying data to a user (e.g., displaying data for observation by the user, audibly communicating data to a user, etc.) as well as receiving inputs from the user (e.g., tactile input, voice instruction, etc.). Accordingly, in one exemplary embodiment, the user interface may include a display (e.g., LCD, etc.) configured to depict visual information and an audio system as well as a keyboard, mouse and/or other input device. Any other suitable apparatus for interacting with a user may also be utilized.

In one embodiment, an individual accesses recovery determination apparatus 12 to attempt to determine their respective state of recovery at the present moment in time. In one example, individuals input data to a respective client 16 on a periodic basis (e.g., daily) and the data is subsequently communicated to server 12. The data may be inputted to apparatus 12 in any suitable manner. For example, a user may manually input data via the user interface 28. In another example, hardware measuring data of the individual (e.g., pulse oximeter) may communicate the data to apparatus 12. As described in further detail below, the data corresponds to one or more recovery marker and may include objective data (e.g., quantitative data of the individual) as well as subjective data (e.g., subjective opinions of the individual).

The apparatus 12 processes the data provided by the individual and determines recovery information which is indicative of the state of recovery of the individual at a moment in time corresponding to the data for the recovery markers. In one embodiment, the apparatus 12 provides the recovery information in the form of a recovery score which may be used to determine the state of recovery of the individual and the individual may use the recovery information to make decisions regarding future training in one example described further below. In one more specific example, the determined recovery score is a numerical representation which is used with predefined ranges of scores to indicate the particular state of recovery of the individual which corresponds to the inputted data for the individual. The recovery information may be communicated to the respective client 16 for viewing or other consumption by the respective individual.

As mentioned above, data regarding one or more recovery marker may be inputted by the individual. Recovery markers pertain to different characteristics of an individual (e.g., different objective and/or subjective parameters or variables regarding the individual) and the inputted data comprises data particular to the individual for the respective recovery markers. In one embodiment, the data is particular to a common moment in time for which the individual desires to determine their state of recovery. Examples of objective and subjective recovery markers are described below.

In one embodiment, it is desired that the data which is inputted by the individual corresponds to a moment in time when the individual is at rest (e.g., at least one hour after the individual has exercised). Accordingly, in one embodiment, the data which is inputted for the recovery markers by the individual corresponds to a period of rest for the individual in between periods of exercise (e.g., in between work-outs of a training plan). Put another way, the individual's data corresponds to measured or determined values for quantitative markers and/or responses for subjective markers while the individual is resting or otherwise within a period of rest for the individual. In addition, the individual may input the data on a periodic basis, for example daily. In one specific example, the individual may input the data at the same time of day (e.g., early in the morning) for consistency.

In one embodiment, the data is processed to provide recovery information including a plurality of marker scores for respective ones of the markers. The marker scores may be combined to provide additional recovery information in the form of a recovery score in one embodiment as described in further below.

A plurality of recovery markers are described below for which the user inputs objective data values or subjective data responses for use in determination of the recovery information for the individual according to one embodiment. These example recovery markers are characteristics which are indicative of a state of recovery of the individual, influence fatigue, have a measurable impact on performance, or are signs or symptoms of overreaching in the described embodiment. In one embodiment described further below, all of these recovery markers are used to calculate the individual's recovery information. In other embodiments, an individual may respond to less than all of the recovery markers. However, it is believed that the greater the number of these recovery markers that an athlete is able to accurately and regularly monitor, the greater the value and validity of the recovery information.

Initially, a plurality of objective/quantitative recovery markers are discussed including resting heart rate, oxygen saturation, body mass and sleep (the sleep recovery marker also includes a subjective component regarding quality of sleep). Thereafter, a plurality of subjective recovery markers are discussed including energy level, mood state, hydration level, previous training performance, well-being, muscle soreness, and appetite. The data inputted for the subjective recovery markers may be self-assessed subjective opinions of the individual with respect to themselves which corresponds to the moment in time when the data for the quantitative recovery markers is ascertained and when the state of recovery is to be determined for the individual in one embodiment. The data for subjective recovery markers may also be quantified objectively in some embodiments. For example, the previous training performance recovery marker may be quantified using objective data of wattage and heart rate in one embodiment. The apparatus 12 may process the individual's data for one or more of the recovery markers to determine the recovery information of the individual in one embodiment. The described recovery markers are example markers used in one embodiment and more, less and/or alternative markers may be used in other embodiments.

In addition, one specific method is described in one embodiment which generates marker scores for respective ones of the recovery markers and calculates a recovery score by combining (e.g., adding) the calculated marker scores. The range of recovery scores is based upon a scale of 100 in the described example. Furthermore, in the following example, the individual marker scores are weighted differently where the weighting (i.e. number of possible points) which an individual recovery marker contributes to the recovery score is based upon the respective recovery marker's predictive reliability (i.e. how well scientific studies have established its correlation is to fatigue). Other recovery markers and/or weightings may be used in other embodiments. Other methods apart from the described example embodiments are possible for determining recovery information. In addition, other methods apart from the following example methods of processing data to calculate marker scores for the individual recovery markers may be used in other embodiments.

The user may provide data for the first recovery marker of resting heart rate using a heart rate sensor or pulse oximeter. Resting heart rate may be monitored during sleep or first-thing in the morning, before getting out of bed in some examples. Day-to-day variations in resting heart rate of approximately 5% are common and not usually associated with fatigue or stress. However, increases of greater than 5% are typically reported in fatigued or acute overreached (sympathetic) individuals.

In the presently described example embodiment, the marker score for the resting heart rate recovery marker may be calculated as a percentage increase of that day's measurement over a baseline. In one embodiment, the baseline may be established from the average of the three-week period ending three days prior to the day of measurement in one example which is sufficiently long to smooth out variations in daily measurement but not sufficiently long that the individual can significantly lower his resting heart rate through training during this time, and creating the risk that an elevated resting heart rate will not be detected. The described example baseline does not include the most recent three days so that if an individual was already in a sympathetic state during the past three days, the baseline will not be artificially increased. The resting heart rate data may be provided by a pulse oximeter in one embodiment.

In one embodiment, the marker score for this resting heart rate recovery marker starts at 20 positive points and the apparatus 12 begins to deduct points when the resting heart rate is elevated by 5%. Points are deducted according to a polynomial equation such that increases of 25% or more result in the loss of 20 points from the overall recovery score in one embodiment. Decreases in resting heart rate do not affect the recovery score. An example formula for determining the marker score once the resting heart rate is elevated by 5% is the cubic equation $0.0009x^3+0.0038x^2+0.0515x+2.6008$ where x is calculated from the individual's inputted data (e.g., x is the percentage of the resting heart rate above the baseline in one example). The apparatus 12 may take twenty minus the output of this formula to determine the marker score in one embodiment. Other methods apart from the explicitly-disclosed example embodiment are possible for determining and using the resting heart rate marker score.

Oxygen saturation may highlight the risk of anemia (decreased number of red blood cells in the blood). Oxygen saturation (SP02) in healthy individuals at sea level or at an altitude to which they have acclimatized is consistently between 95% and 99%. Oxygen saturation below 90% may indicate anemia, which is usually associated with weakness or fatigue. Readings below this level may indicate that the body is stressed from adapting to altitude, may be an early sign of anemia (decreased number of red blood cells in the blood), or may indicate the onset of other illnesses such as influenza, incipient bronchitis or some form of cellular perfusion compromise.

An individual may use a pulse oximeter to determine their oxygen saturation which may be inputted by the individual into the apparatus 12 for use in calculating the marker score for oxygen saturation. Because a normal SP02 reading is not a positive indicator of recovery, the SP02 marker score is zero or negative in the described example embodiment and it cannot contribute positive points. In one specific example, points are deducted when the SP02 reading is below 95%, and it deducts points on a linear scale until 10 points are deducted for readings of 90% or lower.

A user may use a calibrated scale to provide data to the apparatus 12 regarding their body mass for use in determining a body mass marker score. Rapid reduction in body mass may occur as a result of fluid and/or substrate loss which may both affect performance. An acute body mass loss of 2% or greater can adversely affect cognitive and physical performance. Regular monitoring of pre-breakfast body mass may aid in optimizing fluid and energy balance.

In one example embodiment, the body mass marker score is calculated as a percentage increase of that day's measurement over a baseline that is established from the mean of the prior week's readings. For example, the apparatus 12 may initially assign five positive points for the body mass marker score and deduct points for decreasing body mass with respect to baseline in one embodiment. In one example, a body mass loss of 0-1% with respect to the baseline results in the loss of 0 points. A body mass loss of 1-2% with respect to the baseline results in the loss of 2 points. A body mass loss of 2-3% with respect to the baseline results in the loss of 3 points. A body mass loss of 3-4% with respect to the baseline results in the loss of 4 points. A body mass loss of >4% with respect to the baseline results in the loss of all 5 points.

In the described example, sleep may also be used as a marker to determine recovery of the individual. Sleep disturbances are common to athletes during periods of high training load or competition. Either, or both, sleep volume (objective) and quality (subjective) can be affected by intense training. Additionally, sub-optimal sleep can lead to compromised recovery. In this way, sleep can be a predictive as well as a diagnostic marker.

In one embodiment, both quantity and quality of sleep are utilized to generate a marker score for sleep. This marker score is calculated as a weighted average of the past three days, with more recent data receiving a heavier weighting in one embodiment. For each night of sleep, a sleep metric score is calculated based on the product of the number of hours slept and the quality of sleep, rated subjectively as "better than normal," "normal," or "worse than normal," with these ratings receiving 5, 3, and 1 points respectively in one embodiment. If this product is greater than 26, the sleep metric is 30; if this product is less than one, the Sleep Metric is 0; if this product is between 1 and 26 inclusive, the sleep metric equals 30−1.2× (26−(the product)) in one embodiment. The formula for determining the total sleep marker score for the present day adds ⅙ the value from three night's prior to ⅓ the value of two night's prior and then to ½ the value of the prior night in one embodiment. This weighting reflects the cumulative effect of sleep on recovery in the described embodiment.

Subjective level of energy is related to physiological, immunological and psychological markers of fatigue. In the described example, an energy level marker score is calculated based upon a response of the individual. In one embodiment, the marker score is based on the user's subjective self-assessment using the scale of "better than normal," "normal," or "worse than normal." Although subjective, this variable has been demonstrated to have a high inverse correlation with fatigue. As such, it contributes 20 positive points for a "normal" rating in one embodiment. An additional eight points are added for a "better than normal" rating, and all points are deducted for a "worse than normal" rating in the described example.

The mood of the individual may also be used to calculate a marker score. General apathy, mood swings, and feelings of depression or anxiety are often indicative of fatigue, illness or overreaching and are commonly associated with underperformance. The mood marker score is based on the user's self-assessment using responses of the individual of "better than normal," "normal," or "worse than normal," in one embodiment. It contributes five positive points for a "normal" rating, an additional point is added for a "better than normal" rating, and all points are deducted for a "worse than normal" rating in one embodiment.

In the described example, hydration level of the individual is also used to calculate a marker score. Pre-training dehydration can compound the effects of prolonged activity on fluid balance. Dehydration of 2% or more can negatively impact cognitive and physical performance and can also affect immune status, body temperature and cardiac output.

In one embodiment, the hydration level marker score is based on the individual's assessment of urine color, where darker colors indicate dehydration and result in score deductions. A urine color chart may be used to provide a useful indication of fasted hydration status. Clear or pale yellow urine earns a hydration level marker score of five positive points, while yellow earns three points, and dark yellow results in a loss of all five points in one example.

Another marker which may be used is previous training performance. Performance is a valid indicator of fatigue or overreaching. Prolonged underperformance is a reliable indicator of overtraining. In the described example, the marker score is based upon the user's subjective self-assessment using the scale of "better than normal," "normal," or "worse than normal." In one embodiment, five positive points are provided for a "normal" rating, an additional point is added for a "better than normal" rating, and all points are deducted for a "worse than normal" rating. If the user did not train the previous day a score of six is assigned in the described embodiment.

Another marker score may be calculated based upon wellbeing of the individual in the described embodiment. Headaches, nausea, diarrhea, and sore throat are all common symptoms of stress, fatigue and illness. Symptoms of upper respiratory tract infections are common to athletes and if prolonged, may indicate overtraining. The wellbeing marker score is determined by the user's indication of the presence or absence of signs of illness in the described embodiment. The absence of these signs earns ten points, while their presence reduces the value to zero in one embodiment.

The apparatus 12 may also calculate a marker score for muscle soreness in one embodiment. Delayed onset of muscle soreness (DOMS) is a normal reaction to high training intensity, which can increase the risk of injury if followed by insufficient rest. Persistent muscle soreness may indicate an increased risk of overuse injury and overtraining syndrome. In the described embodiment, the muscle soreness marker score is determined by the user's indication of the presence of muscle soreness. The absence of soreness earns a marker score of five points while its presence reduces the value to zero in one example.

Appetite is also used as a marker score in one embodiment. Appetite typically decreases with high training load and fatigue, which can result in negative energy balance. Inadequate carbohydrate intake can lead to earlier onset of overreaching symptoms and impaired performance, while insufficient protein and micronutrient intake may have a direct impact on immune function, protein synthesis and recovery from training. The appetite marker score is determined by the user's self-assessment of appetite. A "normal" appetite earns five points while a suppressed appetite reduces the value to zero in one embodiment.

Recovery information may be determined following entry of data for individual ones of the recovery markers by the individual. In one embodiment, the apparatus 12 uses the data inputted by the individual to calculate a plurality of marker scores for individual ones of the recovery markers. In one example embodiment, the marker scores for all of the markers are summed and in the above-described example, there are a total of 120 possible points. In one embodiment, the apparatus 12 divides the sum of the marker scores by 1.2 to determine the recovery score on a scale of 0-100 for the day corresponding to the data entered by the user. In another example, each of the marker scores may be divided by 1.2 and thereafter summed together to determine the recovery score. Some example embodiments of graphical representations of recovery information are discussed below with respect to FIGS. 4-5.

Figure 3:
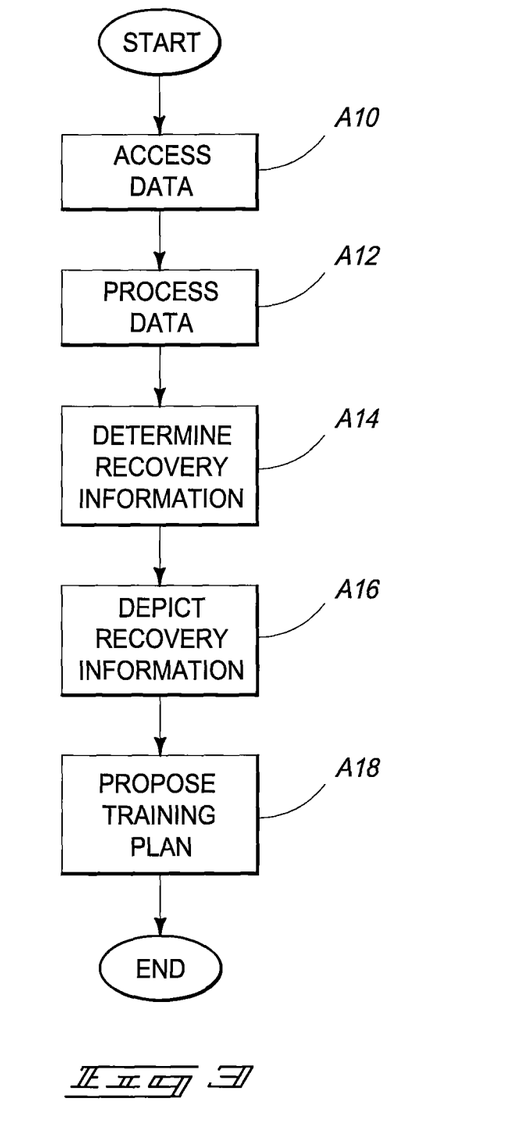
FIG. 3 is a flow chart of one method of determining recovery of an individual according to one embodiment.

Referring to FIG. 3, a method for determining recovery information of an individual is illustrated according to one embodiment. The depicted method may be implemented by computing device 20 which may be embodied as a server in the example arrangement of FIG. 1, a personal computer of the individual in another arrangement, or in any other suitable arrangement. Other methods are possible including more, less and/or alternative acts.

At an act A10, the apparatus accesses inputs for the individual. The accessed inputs may include data pertinent to the individual at a desired interval (e.g., every morning) and include data regarding one or more recovery marker for the individual when the data is entered. The data of the inputs for the individual for a given interval correspond to a moment in time when the user is at rest (e.g., a resting period between periods of exercise in one example) and pertain to a moment in time for which the state of recovery for the individual is to be determined. The data may include objective data (e.g., quantitative data) and subjective data as discussed above.

At an act A12, the apparatus processes the data of the inputs of the individual. In one embodiment, the data of the inputs correspond to one or more of a plurality of different recovery marker(s) and the data of the inputs are processed for use in determination of the recovery information.

At an act A14, the apparatus determines recovery information which is indicative of a state of recovery of the individual using the processing of the data. In one embodiment, the data accessed by the apparatus is processed into recovery information in the form of one or more marker scores which may be combined to generate additional recovery information in the form of a recovery score which is indicative of the state of recovery of the individual for the day when the data is entered. In one more specific example, the apparatus sums the marker scores to determine the recovery score. The individual may utilize the recovery score to make decisions regarding future training in one embodiment (e.g., whether or not to train and an appropriate level of training).

Figure 4:
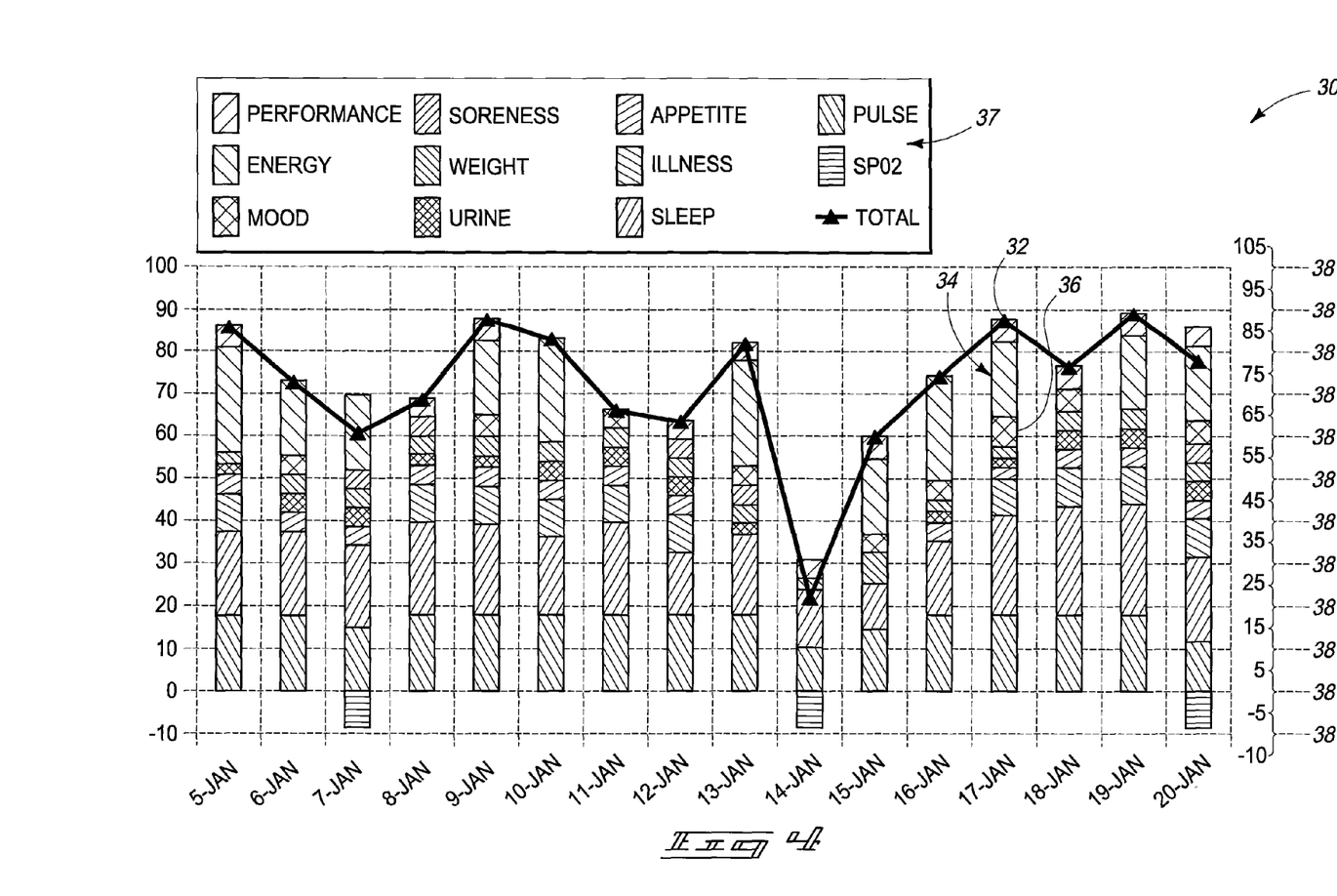
FIG. 4 is a graphical representation of recovery of an individual according to one embodiment.
Figure 5:
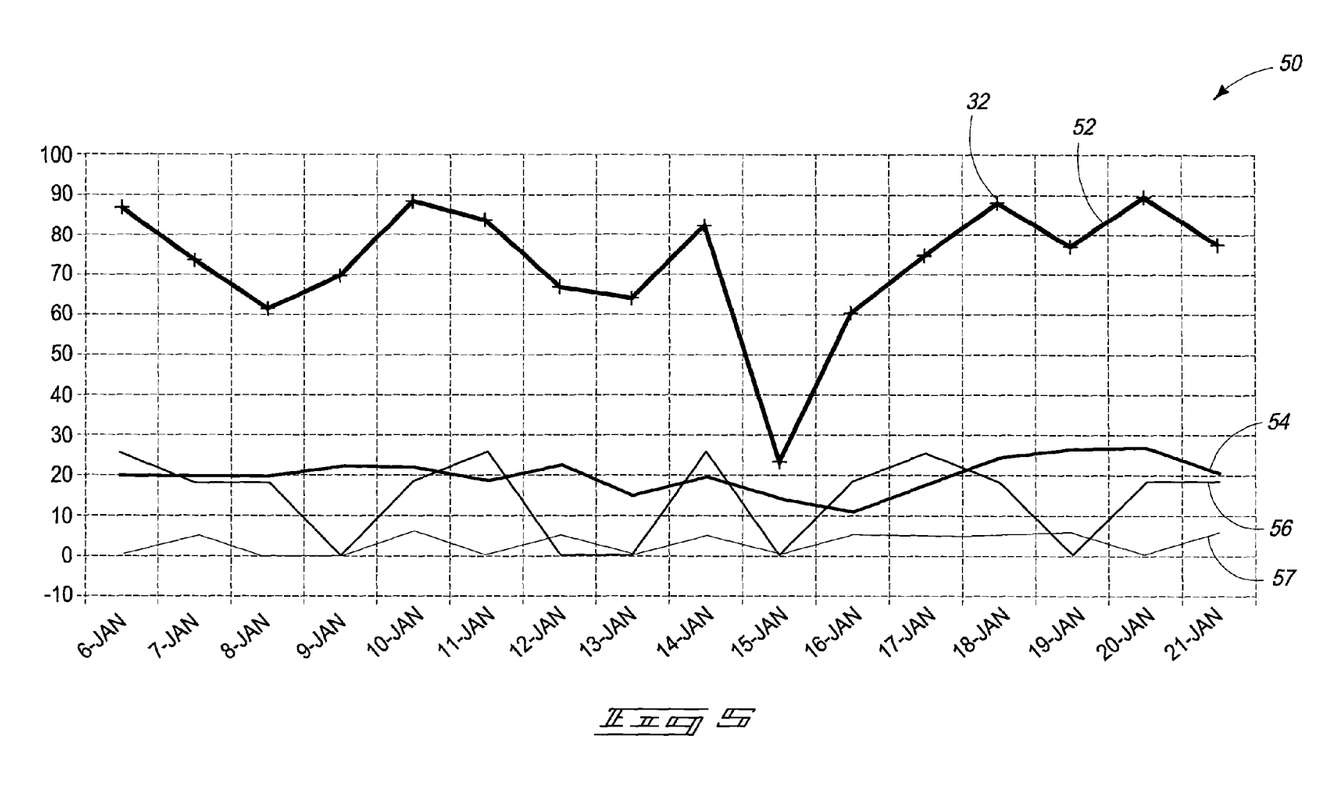
FIG. 5 is a graphical representation of recovery of an individual according to one embodiment.

At an act A16, the recovery information may be depicted for example as shown in FIGS. 4 and 5. In addition, one or more of the marker scores may be selected by a user for depiction using the apparatus. The recovery information may be conveyed to the individual in any suitable manner.

At an act A18, the apparatus may propose a plan for future training for the individual based upon the calculated recovery score in one embodiment. For example, the apparatus may propose that the individual has reached a sufficient level of recovery from previous exercise and can proceed to train in one example. In another example, the apparatus may provide a plan that advises that the individual has not yet reached a sufficient level of recovery and the individual should rest based upon the recovery score.

Referring to FIG. 4, one embodiment of a visual representation of recovery information is shown in the form of an example graph 30. The visual representations may be depicted using a user interface of the computing device in one embodiment. Other visual representations for depicting recovery information may be used in other embodiments.

The illustrated graph 30 illustrates a two-week time frame on the x-axis and a recovery score scale on the y-axis. A plurality of recovery scores 32 are shown corresponding to individual days in the depicted embodiment. A plurality of bars 34 are also shown corresponding to the recovery scores 32. Individual ones of the bars 34 include a plurality of portions 36 which correspond to respective ones of the recovery markers indicated by the legend 37 which may be different colors in one embodiment. In one embodiment, the sizes of the portions 36 correspond to the values of the respective marker scores for the recovery markers and which were calculated based upon the data inputted by the individual. The marker scores are positive values except for oxygen saturation (SpO2) in the illustrated example. The illustration of the portions 36 of different sizes depicts the different contributions of the individual marker scores for the recovery markers to the recovery score in one embodiment. Some of the bars 34 include less than all of the possible recovery markers indicating that the individual did not provide data for the recovery marker or the marker score for the recovery marker was zero for the given day for the individual. The individual marker scores have been divided by 1.2 prior to summations to determine the respective recovery scores 32 in the depicted embodiment.

The recovery information may be used to identify one of a plurality of different states or levels of recovery of an individual (i.e., quantify the level of recovery) in one embodiment. As mentioned above in one example, the recovery information may be provided in terms of a recovery score 32. Recovery score 32 is within a scale of 0-100 in the described embodiment. The y-axis may be divided into a plurality of portions 38 to facilitate an individual's understanding of the recovery scores 32 in one embodiment. The individual portions 38 correspond to different ranges of recovery scores (e.g., 95+, 95-85, 85-75, 75-65, etc.) and which indicate different states or levels of recovery for the individual in one embodiment. In one implementation, the portions 38 may be color coded to facilitate the individual's understanding of the recovery scores. In one specific example, the upper most portion 38 corresponding to "fully recovered" recovery scores of 95+ may be dark green while the lowest most portion corresponding to "overtrained" recovery scores of 5 or below may be dark red. The intermediate portions 38 may transition from dark green to dark red for ease in reading the results of the graph 30. Other display embodiments are possible, including for example, using different colors for individual ones of the portions 38.

The recovery scores and different levels of recovery may be used to propose a plan of future training for the individual in one embodiment. For example, for recovery scores >=95: the apparatus may indicate that the individual is fully recovered and may implement full training. Recovery scores of >=85 may indicate that the individual's recovery is almost complete and they are ready to train. Recovery scores of >=75 may indicate that the individual is showing minor signs of reduced recovery, but the individual seems to be absorbing the current training load well. Recovery scores of >=65 may indicate that the individual is showing signs of reduced recovery or having difficulty in maintaining the current training load and may advise the individual to proceed training with caution. Recovery scores of >=55 may indicate that the individual is not sufficiently recovered or the individual is over-reaching and the individual should consider resting. Recovery scores of >=45 may indicate that the individual is not recovering sufficiently and rest is strongly recommended. Recovery scores of >=35 may indicate that even if the individual is intentionally over-reaching, the individual has probably pushed themselves too hard and they should rest for a few days. Recovery scores of >=25 may indicate that the individual's recovery is substantially depressed and continued exercise will likely lead to overtraining, illness or injury. Recovery scores of >=15 may indicate that several systems are over stressed and the individual is advised to consult with a medical professional before continuing training. Recovery scores of <15 may indicate that the individual is showing multiple signs of overtraining and a medical professional should be consulted as soon as possible.

Referring to FIG. 5, another visual representation of recovery information is shown in one example embodiment in the form of a graph 50. Graph 50 depicts a line 52 which corresponds to recovery scores 32 without the depiction of the bars 34 of FIG. 4. In addition, a plurality of lines 54, 56, 57 corresponding to the respective markers scores for the recovery markers sleep, energy and mood are also shown. The format of graph 50 shows the contribution of three recovery markers to the recovery scores 32 in one embodiment. More, less and/or alternative marker scores may also be selected by the individual for display relative to the line 52 for the recovery scores 32.

In one embodiment, the recovery information provided by the apparatus is a useful component of a coherent training program, as athletes may rely on it to understand how they are responding to a training load. The recovery information may be used in a number of ways including training plan optimization where the goal is structuring a long-range training plan to introduce an athlete to training loads that are effective in improving performance, and to balance these loads with recovery for the athlete's body to adapt to the stimulus. During this example process—known as "periodization"—an athlete goes through several stages of training load, or "phases" and these stages range from undertraining during the period between competitive seasons or during active rest/taper, to overreaching, a phase which will feature poor adaptation and diminished competitive performance.

Although periods of overreaching are necessary to introduce conditions for positive physiological adaptation, when prolonged, these periods may coincide with other stressors and insufficient recovery may ensue. Performance decrements may result in chronic maladaptations, leading eventually to overtraining syndrome (OTS). In other words, successful training involves stimulus overload while avoiding the combination of excessive training and inadequate recovery. The recovery information described herein may assist athletes and coaches with making informed, intelligent decisions within the context of their training plans. By expressing an athlete's state of recovery, the recovery information may help an athlete maximize the results from each training session, and may provide information regarding the magnitude and frequency of the periodization cycles within a training plan.

It is believed that aspects of the disclosure for providing recovery information offer benefits to various individuals including, for example, coaches seeking to understand their athlete's bodies (supervision), to athletes who seek to maximize performance at a target date in the future (self-direction), to athletes who don't understand what it is like to be over-trained (education) and to athletes seeking to pursue performance after an extended period of time off (re-calibration).

The recovery information may also be used for injury prevention in one aspect. For example, four causes of mechanical injuries arise from participation in sports. With the notable exception of blunt trauma (e.g., as a result of a collision), the causes can be traced to the relationship between training stimulus and recovery. For example, soft tissue damage occurs through direct or indirect trauma to muscles, ligaments, and joint capsules. Direct trauma refers to an injury occurring from sudden overload, and is known as macrotrauma, i.e., true muscle tear or ligament sprain. In contrast, indirect trauma results from repeated submaximal loading, leading to clinical signs and symptoms.

Injury presents itself in three stages: acute, subacute/overuse, and acute/chronic. The acute stage of direct trauma stems from sudden overloading, or macrotrauma (e.g. a 100 meter runner exploding out of the starting blocks), and often occurs during competition when athletes push themselves beyond the levels achieved during training. Muscle pulls, torn connective tissue, extreme dehydration and psychological trauma can all be experienced by athletes who push themselves to their absolute limits during competition.

The risk of injury is increased among athletes in two scenarios which the recovery information provided herein may help athletes avoid. In the first scenario, the athlete has not recovered adequately from training to let their connective tissue repair itself completely before the competition, leaving it more vulnerable to injury. Over time, the recovery information provided herein in one aspect helps athletes reduce this risk by letting them know how much rest they need to recover fully between training and competition. In the second scenario, the athlete has not prepared adequately for the increased load of competition. The recovery information may be used to indicate to an athlete that they are consistently "too recovered" (i.e. not training hard enough) during the preparation period for a key event, or if they have not completed enough hard training to support an increase in training load.

The subacute/overuse stage occurs when increased training stimulus load combines with insufficient recovery within a periodization cycle. Excessive cumulative loading can degenerate body tissues leading to microtrauma of connective and muscular tissue and an accompanying inflammatory response (e.g. Achilles tendinitis in the endurance athlete or runner), and to compromised cardiovascular components. This may in turn lead to catastrophic failure of the musculoskeletal structure, or chronic cardiovascular fatigue. Ironically, these types of overtraining injuries are frequently seen in the months following an athlete's increase in training capacity. As fitness increases, so does training appetite. But the body can require a surprisingly long time to respond to increased training loads (few athletes can absorb annual increases greater than 10%). The recovery information provided herein may in one aspect be used to help athletes understand how well they are adapting to increased training loads, which will lead to confident, informed decisions about when to increase load and when to allow body tissues to recuperate.

The chronic stage results from insufficient recovery during extended periods of incremental over-reaching. Since periodic over-reaching is used for positive adaptation, the risk of chronic over-reaching is high. Problematically, if an athlete undergoes extended high volumes of training, performance will be compromised even though fitness will increase. In the absence of an objective measure of their state of recovery, an athlete will be unaware of this emerging risk, as their increased fitness will mask, for some time, suboptimal performance. After several months of this condition, chronic over-use injuries such a tendonosis, tendonitis, aggravated intra-muscular swelling, bursitis, and many others may develop. Beyond over-reaching, which at times will be intentional, lies the state known as "over training syndrome". For any athlete, OTS is catastrophic, and can require months, if not years, for full recovery. It is logical to conclude that if an athlete were to avoid a condition of chronic over-reaching, then OTS will not be possible. The recovery information may be used to identify incipient chronic over-reaching long before an athlete begins to experience the symptoms associated with it in one aspect.

The recovery information may also be used for illness prevention in one aspect. For example, in addition to injury from tissue damage and cardiovascular fatigue, athletes who train chronically without adequate recovery risk the deterioration of various wellbeing markers. These include persistent upper respiratory tract infections, low-grade anemia, bronchitis, neuro-muscular disorders, arrhythmia, and a wide variety of illnesses not commonly associated with otherwise "healthy" and active athletes. By consistently monitoring the recovery information, an athlete will be able to avoid chronic over-reaching that leads to these health complications.

The apparatus and methods described herein enable individuals to determine their state of recovery from previous exertion by entering data and without going to a laboratory. Athletes may use the recovery information to determine his or her actual state of recovery, and to maximize the efficacy of their training in one embodiment. In one example use, the recovery information may be used to ensure that the athlete has sufficiently recovered from prior stimulus so they are ready to extract the maximum benefit from subsequent efforts. Other times, the recovery information may be used for monitoring intentional "over-reaching" conditions where repeated workouts without adequate recovery are performed so when the athlete finally rests, the body "supercompensates" and takes an incremental leap in fitness, for example, before a key athletic competition. Using the recovery information to provide information regarding an individual's state of recovery gives athletes a clear view of their physiological response to training stimulus. The recovery information herein may be used to help athletes shape the contours of a coherent, intelligent training plan as described above in one embodiment.

In compliance with the statute, the invention has been described in language more or less specific as to structural and methodical features. It is to be understood, however, that the invention is not limited to the specific features shown and described, since the means herein disclosed comprise preferred forms of putting the invention into effect. The invention is, therefore, claimed in any of its forms or modifications within the proper scope of the appended claims appropriately interpreted in accordance with the doctrine of equivalents.

Further, aspects herein have been presented for guidance in construction and/or operation of illustrative embodiments of the disclosure. Applicant(s) hereof consider these described illustrative embodiments to also include, disclose and describe further inventive aspects in addition to those explicitly disclosed. For example, the additional inventive aspects may include less, more and/or alternative features than those described in the illustrative embodiments. In more specific examples, Applicants consider the disclosure to include, disclose and describe methods which include less, more and/or alternative steps than those methods explicitly disclosed as well as apparatus which includes less, more and/or alternative structure than the explicitly disclosed structure.

What is claimed is:

1. A recovery determination method comprising:
accessing a plurality of inputs for a plurality of different recovery markers which correspond to a plurality of different characteristics of an individual, wherein the inputs comprise data pertinent to the individual for the respective recovery markers while the individual is at rest following a period of exercise by the individual;
using processing circuitry, processing the data of the individual for the recovery markers including weighting the data for the different recovery markers differently corresponding to different predictive reliabilities of the different recovery markers as being indicative of fatigue of the individual; and
using processing circuitry, determining recovery information which is indicative of a state of recovery of the individual using the processing of the data.

2. The method of claim 1 wherein the determining recovery information comprises calculating a recovery score which indicates one of a plurality of different states of recovery for the individual.

3. The method of claim 1 wherein at least one of the accessed inputs is based upon a self-assessed subjective opinion of the individual with respect to themselves at a moment in time when the state of recovery is to be determined.

4. The method of claim 1 wherein the processing comprises, using the data for the different recovery markers, determining a plurality of marker scores which correspond to respective ones of the different recovery markers using a plurality of different weightings which correspond to the different predictive reliabilities of the different recovery markers as being indicative of fatigue of the individual, and wherein the determining comprises determining a recovery score using the marker scores.

5. The method of claim 4 further comprising generating a visual representation of the recovery score and an individual one of the marker scores.

6. The method of claim 5 wherein the visual representation depicts contributions of the marker scores to the recovery score.

7. The method of claim 1 further comprising, using the determined recovery information, proposing a plan regarding training of the individual in the future.

8. The method of claim 1 wherein one of the accessed inputs comprises a number of heart beats for one of the recovery markers which is a resting heart rate for the individual.

9. The method of claim 1 wherein the weighting comprises weighting the data of one of the recovery markers to contribute an increased amount to the recovery information compared with weighting the data of another of the recovery markers as a result of the one recovery marker having an increased predictive reliability as being indicative of fatigue of the individual compared with the another recovery marker.

10. The method of claim 1 further comprising selecting the different recovery markers based upon the predictive reliabilities of the different recovery markers as being indicative of fatigue of the individual.

11. A recovery determination method comprising:
accessing a plurality of inputs for respective ones of a plurality of different recovery markers which correspond to respective ones of a plurality of different characteristics of an individual, wherein the inputs comprise data pertinent to the individual for respective ones of the recovery markers;
using processing circuitry, processing the data for the respective ones of the recovery markers including weighting the data for the different recovery markers differently corresponding to different predictive reliabilities of the different recovery markers as being indicative of fatigue of the individual;

using the processing, determining recovery information regarding a state of recovery of the individual; and wherein the data of one of the recovery markers comprises objectively measured data, and the determining comprises combining the objectively measured data with data of another of the recovery markers which is a subjective opinion of the individual.

12. The method of claim 11 wherein the inputs comprise the data regarding the individual at a moment in time when the individual is at rest following a period of exercise.

13. The method of claim 11 wherein the recovery markers are different indicators of fatigue in the individual.

14. The method of claim 11 wherein the data of the one recovery marker is indicative of a percentage increase of a resting heart rate for the individual over a baseline of the resting heart rate for the individual.

15. The method of claim 11 wherein the determining the recovery information comprises determining without the use of any data which was acquired during sleep of the individual.

16. The method of claim 11 wherein the data of the another recovery marker is indicative of a well-being of the individual.

17. A recovery determination apparatus comprising:
an interface configured to receive a plurality of inputs for a plurality of different recovery markers which correspond to a plurality of characteristics of an individual, wherein the inputs comprise data pertinent to the individual for the recovery markers while the individual is at rest following a period of exercise by the individual; and
processing circuitry coupled with the interface and configured to:
access the data for the recovery markers;
process the data for the recovery markers; and
using a result of the processing, determine recovery information which is indicative of a state of recovery of the individual; and
wherein the processing circuitry is configured to process the data for the different recovery markers by weighting the data for the different recovery markers differently corresponding to different predictive reliabilities of the different recovery markers as being indicative of fatigue of the individual.

18. The apparatus of claim 17 wherein the processing circuitry is configured to use the data for the different recovery markers to determine a plurality of marker scores for respective ones of the different recovery markers and to determine a recovery score using the plurality of marker scores.

19. The apparatus of claim 17 wherein the interface receives the data for the different recovery markers which pertain to a moment in time when the individual is at rest following the period of exercise by the individual.

* * * * *